(12) United States Patent
Iijima et al.

(10) Patent No.: US 9,790,154 B2
(45) Date of Patent: Oct. 17, 2017

(54) METHANOL PLANT AND GASOLINE SYNTHESIS PLANT

(71) Applicant: MITSUBISHI HEAVY INDUSTRIES, LTD., Tokyo (JP)

(72) Inventors: Masaki Iijima, Tokyo (JP); Haruaki Hirayama, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/769,190

(22) PCT Filed: Feb. 26, 2014

(86) PCT No.: PCT/JP2014/054672
§ 371 (c)(1),
(2) Date: Aug. 20, 2015

(87) PCT Pub. No.: WO2014/141883
PCT Pub. Date: Sep. 18, 2014

(65) Prior Publication Data
US 2015/0376097 A1    Dec. 31, 2015

(30) Foreign Application Priority Data
Mar. 11, 2013    (JP) ................................. 2013-048021

(51) Int. Cl.
*B01J 19/00*    (2006.01)
*B01J 19/24*    (2006.01)
(Continued)

(52) U.S. Cl.
CPC ................ *C07C 31/04* (2013.01); *B01D 1/26* (2013.01); *B01D 3/007* (2013.01); *B01D 3/146* (2013.01);
(Continued)

(58) Field of Classification Search
CPC . B01J 19/00; B01J 19/24; B01J 19/245; B01J 2219/00–2219/00004; C07C 29/00;
(Continued)

(56) References Cited

U.S. PATENT DOCUMENTS 4,134,732 A * 1/1979 Jackson ................. B01D 3/143
114/26
4,709,113 A 11/1987 Harandi et al.
(Continued)

FOREIGN PATENT DOCUMENTS

JP    63-275691 A    11/1988
JP    3-506046 A    12/1991
(Continued)

OTHER PUBLICATIONS

Machine translation of JP 2005-035967 A, which was provides with IDS filed Aug. 20, 2015 and published on Feb. 10, 2005.*
(Continued)

*Primary Examiner* — Natasha Young
(74) *Attorney, Agent, or Firm* — Westerman, Hattori, Daniels & Adrian, LLP (57) ABSTRACT

Provided is a methanol plant that can obtain fresh water from sea water by using, in a seawater desalination device, the exhaust heat discharged in a step for producing methanol from natural gas. The methanol plant is provided with: a heat exchanger (4) that recovers into a thermal medium (for example, seawater) the exhaust heat discharged from a step for producing methanol from a feed stock (for example, natural gas); and a seawater desalinization device (6) that obtains freshwater from seawater using the exhaust heat recovered by means of the thermal medium.

12 Claims, 4 Drawing Sheets

(51) Int. Cl.
| | |
|---|---|
| C07C 29/00 | (2006.01) |
| C07C 29/15 | (2006.01) |
| C07C 29/151 | (2006.01) |
| C07C 29/152 | (2006.01) |
| C07C 31/00 | (2006.01) |
| C07C 31/02 | (2006.01) |
| C07C 31/04 | (2006.01) |
| C10G 3/00 | (2006.01) |
| C02F 1/16 | (2006.01) |
| B01D 1/26 | (2006.01) |
| B01D 3/00 | (2006.01) |
| B01D 3/14 | (2006.01) |
| C02F 1/06 | (2006.01) |
| C02F 1/00 | (2006.01) |
| C02F 1/02 | (2006.01) |
| C02F 1/04 | (2006.01) |
| B01D 1/00 | (2006.01) |
| C02F 103/08 | (2006.01) |

(52) U.S. Cl.
CPC ............ *B01J 19/24* (2013.01); *B01J 19/245* (2013.01); *C02F 1/06* (2013.01); *C02F 1/16* (2013.01); *C07C 29/152* (2013.01); *C10G 3/00* (2013.01); *B01J 2219/0004* (2013.01); *B01J 2219/24* (2013.01); *C02F 2103/08* (2013.01); *C10G 2400/02* (2013.01); *Y02P 20/124* (2015.11); *Y02P 30/20* (2015.11); *Y02P 70/34* (2015.11)

(58) Field of Classification Search
CPC ..... C07C 29/15; C07C 29/151; C07C 29/152; C07C 31/00–31/04; C02F 1/00; C02F 1/02; C02F 1/04; C02F 1/06; C02F 1/16; C02F 2103/00; C02F 2103/08; B01D 1/00; B01D 1/26; B01D 3/00; B01D 3/14; B01D 3/143; B01D 3/146; C10G 3/00; C10G 2400/00; C10G 2400/02; Y02P 20/00–20/122; Y02P 20/124; Y02P 30/00; Y02P 30/20; Y02P 70/00; Y02P 70/10; Y02P 70/34

See application file for complete search history.

(56) References Cited

U.S. PATENT DOCUMENTS

| | | | |
|---|---|---|---|
| 4,830,635 A | 5/1989 | Harandi et al. | |
| 2003/0168864 A1* | 9/2003 | Heronemus | ............ B63B 35/44 290/55 |
| 2004/0219400 A1* | 11/2004 | Al-Hallaj | ................ C02F 1/041 429/424 |
| 2010/0036186 A1 | 2/2010 | Joensen et al. | |

FOREIGN PATENT DOCUMENTS

| | | | |
|---|---|---|---|
| JP | 7-138198 | A | 5/1995 |
| JP | 9-1127 | A | 1/1997 |
| JP | 11-269109 | A | 10/1999 |
| JP | 2001-39911 | A | 2/2001 |
| JP | 2005-35967 | A | 2/2005 |
| JP | 2005-336076 | A | 12/2005 |
| JP | 2006-51451 | A | 2/2006 |
| JP | 2006-70889 | A | 3/2006 |
| JP | 2007-326426 | A | 12/2007 |
| JP | 2010-512435 | A | 4/2010 |
| JP | 2013-147533 | A | 8/2013 |
| JP | 2014-84265 | A | 5/2014 |
| WO | 2011/148422 | A1 | 12/2011 |

OTHER PUBLICATIONS

International Search Report dated Apr. 28, 2014, issued in counterpart Application No. PCT/JP2014/054672 (2 pages).
English translation of Written Opinion dated Apr. 28, 2014, issued in counterpart Application No. PCT/JP2014/054672 (4 pages).
Notice of Acceptance dated Aug. 29, 2016, issued in counterpart Australian Application No. 2014231976. (3 pages).

\* cited by examiner

METHANOL PLANT AND GASOLINE SYNTHESIS PLANT

TECHNICAL FIELD

The present invention relates to methanol plant for producing methanol which is a synthesis gas from natural gas, and a plant for synthesizing gasoline with methanol as a feed stock.

BACKGROUND ART

In a methanol plant, a synthesis gas (for example, methanol) is produced from a feed stock (for example, natural gas). In a case of synthesizing methanol from natural gas, in general, a reformed gas which includes hydrogen and carbon monoxide is produced by steam-reforming natural gas, and methanol is synthesized from the gas.

In a case of synthesizing methanol or methanol-via gasoline from natural gas, natural gas and water (fresh water) are required as a feed stock. However, in such a methanol plant, there is a problem in that fresh water is very scarce in a desert area of the Middle East, North Africa, or the like, or an area such as the North Pole.

In a case of synthesizing methanol or methanol-via gasoline from natural gas, since fresh water is required, a technique of obtaining fresh water from seawater or brine by desalinated seawater or brine is known. In order to perform the desalination, PTL 1 discloses a production apparatus of fresh water from seawater or brine, in which evaporation (flash) is performed by heating seawater or brine and cooling is performed again, thereby obtaining fresh water.

CITATION LIST

Patent Literature

[PTL 1] Japanese Unexamined Patent Application Publication No. 9-1127

SUMMARY OF INVENTION

Technical Problem

In a seawater desalination device as shown in PTL 1, in general, distillation under reduced pressure is performed in order to make thermal efficiency better. Further, in the actual plant, a large number of decompression chambers are combined. This system is called a multistage flash evaporation system. It is possible to produce a large amount of fresh water by the evaporation system. In this evaporation method, for example, it is necessary to heat seawater or brine to a temperature close to 90° C., and thus there is a problem in that fossil fuel such as natural gas is consumed in large amounts. Further, due to burning much fossil fuel, there is a problem in that carbon dioxide is generated.

Further, exhaust heat discharged in a process of synthesizing methanol from natural gas is cooled by a cooling fan or the like, because a synthesis gas which contains much moisture is condensed by cooling. The cooling fans are provided in various places, and therefore, there is a problem in that a large amount of energy is discarded.

The present invention has been made in view of such circumstances and has an object to provide a methanol plant and a gasoline synthesis plant in which it is possible to effectively utilize exhaust heat discharged in a process of producing methanol from natural gas.

Solution to Problem

In order to solve the above problems, a methanol plant according to the present invention adopts the following means.

A methanol plant according to a first aspect of the present invention includes: a heat exchanger which utilizes exhaust heat which is discharged from a process of producing methanol from a feed stock; and a seawater desalination device which obtains fresh water from seawater or brine by using the exhaust heat.

In a process of producing methanol as a synthesis gas from a feed stock (for example, natural gas), exhaust heat is generated. A heat exchanger which makes the exhaust heat be recovered to a thermal medium is provided, and heat exchange is performed between seawater or brine flowing through the heat exchanger and a gas which is in a methanol production process. The exhaust heat recovered to seawater or brine by the heat exchanger is supplied to the seawater desalination device, whereby it is possible to desalinate seawater or brine. In this manner, the exhaust heat is utilized as a heat source of the seawater desalination device, whereby it is possible to eliminate costs of fuel which is used in the seawater desalination device.

Further, in the methanol plant according to the first aspect, the exhaust heat may have a temperature in a range of 100° C. to 200° C.

The exhaust heat which is recovered by the heat exchanger has a temperature in a range of 100° C. to 200° C. The exhaust heat in this temperature range has been discarded without being utilized in the related art. However, the exhaust heat is recovered and utilized as a heat source for desalinated seawater or brine by focusing on the fact that the exhaust heat can be effectively utilized when desalinated seawater or brine.

Further, in the methanol plant according to the first aspect, a plurality of the heat exchangers may be provided in a flow direction of a synthesis gas which is in the process of producing methanol.

A plurality of heat exchangers are provided in the flow direction of the synthesis gas which is in the process of producing methanol. Heat exchange is performed between seawater or brine and the synthesis gas which is in the process of producing methanol, by these heat exchangers. The synthesis gas which is in the process of producing methanol passes through the plurality of heat exchangers, whereby the exhaust heat is recovered, and thus a temperature decreases. In a case where the temperature of the synthesis gas decreases, the temperature falls below the dew point of moisture in the synthesis gas, and therefore, the wetness of the gas increases as it flows toward the downstream side in the flow direction of the synthesis gas. In this way, it is possible to perform heat exchange with the synthesis gas having higher wetness as it goes toward the heat exchanger provided on the downstream side in the flow direction of the synthesis gas which is in a manufacturing process. As compared to a case of performing heat exchange between a dry gas having wetness of 0 and seawater or brine, the wettability of a heat-exchange pipe provided in the heat exchanger increases, and thus it is possible to improve a heat exchange property. Therefore, a heat exchange property can be improved as it approaches the downstream side in the flow direction of the gas which is in a methanol production process. In this way, it is possible to improve exhaust heat recovery efficiency. Further, it is possible to improve heat exchange efficiency, and therefore, it is possible to reduce the size of the heat exchanger.

Further, in the methanol plant according to the first aspect, the seawater desalination device may obtain fresh water by a multistage flash evaporation method using the exhaust heat.

The exhaust heat obtained from the gas which is in a synthesis gas production process is supplied to the seawater desalination device using a multistage flash evaporation method. In this way, it is possible to obtain fresh water from seawater or brine. Since it is not necessary to manufacture a heat source for evaporating seawater or brine, it is possible to eliminate fuel costs.

Further, in the methanol plant according to the first aspect, the methanol may be produced by using vapor which is produced from the fresh water.

The fresh water obtained by the seawater desalination device is supplied to the process of producing methanol from a feed stock (for example, methanol synthesis). In this way, the fresh water produced from only exhaust heat can be used in a water supply for process steam for methanol synthesis.

Further, in the methanol plant according to the first aspect, the process may be provided with a step of producing gasoline from the methanol.

In the step of producing gasoline, heat having been used for the distillation of methanol becomes unnecessary. Therefore, it is possible to utilize exhaust heat of a distillation system which is unnecessary.

A gasoline synthesis plant according to a second aspect of the present invention includes: a methanol plant which produces methanol from a feed stock; a heat exchanger which makes exhaust heat that is discharged from a process of producing gasoline from the methanol be recovered to seawater; and a seawater desalination device which obtains fresh water from the seawater by using the exhaust heat recovered by the seawater.

A distillation system which distills methanol is not required in the case of gasoline synthesis. Therefore, exhaust heat having been used in the distillation system can be supplied to the seawater desalination device. In this way, it is possible to produce a larger amount of fresh water, as compared to a methanol plant. Further, it is possible to not only supply water which is necessary for methanol synthesis, but also supply water to a peripheral area which is poor in a water source.

Advantageous Effects of Invention

According to the present invention, in a process of producing methanol as a synthesis gas from a feed stock (for example, natural gas), exhaust heat is generated. A heat exchanger which makes the exhaust heat be recovered to seawater is provided, and heat exchange is performed between seawater or brine flowing through the heat exchanger and a gas which is in a methanol production process. The exhaust heat recovered to seawater by the heat exchanger is supplied to the seawater desalination device, whereby it is possible to desalinate seawater or brine. In this manner, the exhaust heat is utilized as a heat source of the seawater desalination device, whereby it is possible to eliminate costs of fuel which is used in the seawater desalination device.

DESCRIPTION OF EMBODIMENTS

First Embodiment

Figure 1:
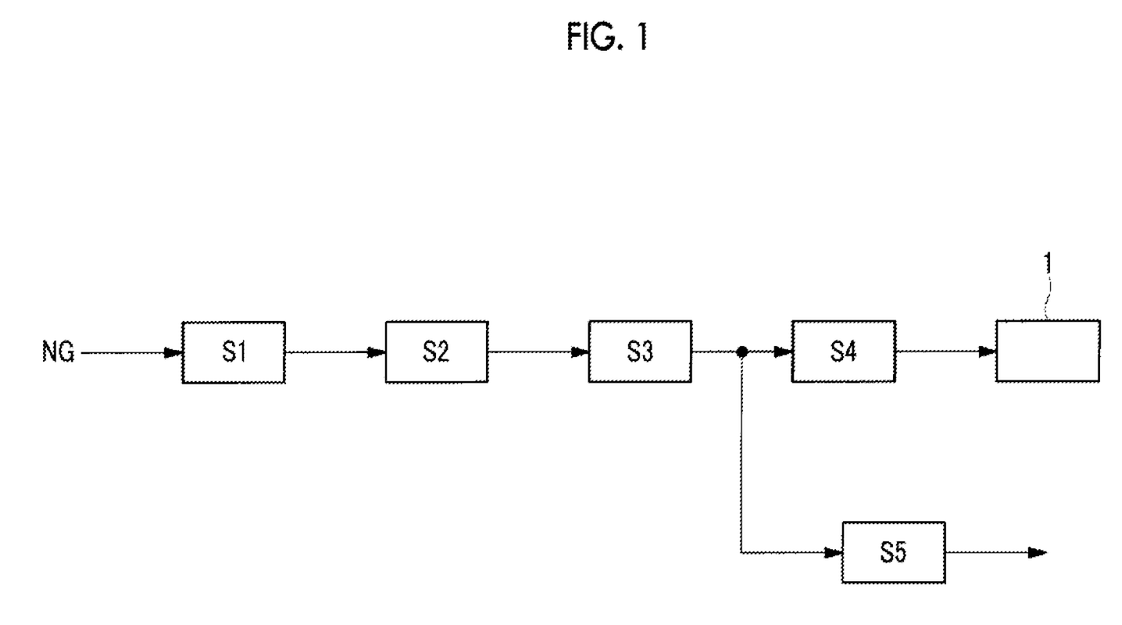
FIG. 1 is a block diagram showing a manufacturing process of a methanol plant according to a first embodiment of the present invention.

A methanol manufacturing process in a methanol plant according to a first embodiment of the present invention is shown in FIG. 1.

First, a feed stock gas (for example, natural gas) is input to a methanol manufacturing plant (a feed stock gas input process S1). Substances (for example, sulfur or the like) which are unnecessary in a reforming process S2 (described later), of the feed stock gas input in the feed stock gas input process S1, are removed by a desulfurization device (not shown). A feed stock gas with the unnecessary substance removed in the desulfurization device is input to a reforming device called a reformer (not shown).

The feed stock gas input to the reformer is mainly methane and is supplied along with water vapor and heated by a combustion exhaust gas of fuel (for example, natural gas), thereby performing a reforming reaction mainly like the following formula, whereby carbon monoxide and hydrogen are generated (the reforming process S2).

$$CH_4+H_2O \rightarrow CO+3H_2$$

The reformer is heated by utilizing exhaust gas heat of the combustion exhaust gas, as described above.

Further, carbon dioxide is also produced by the following reaction.

$$CH_4+2H_2O \rightarrow CO_2+4H_2$$

Figure 2:
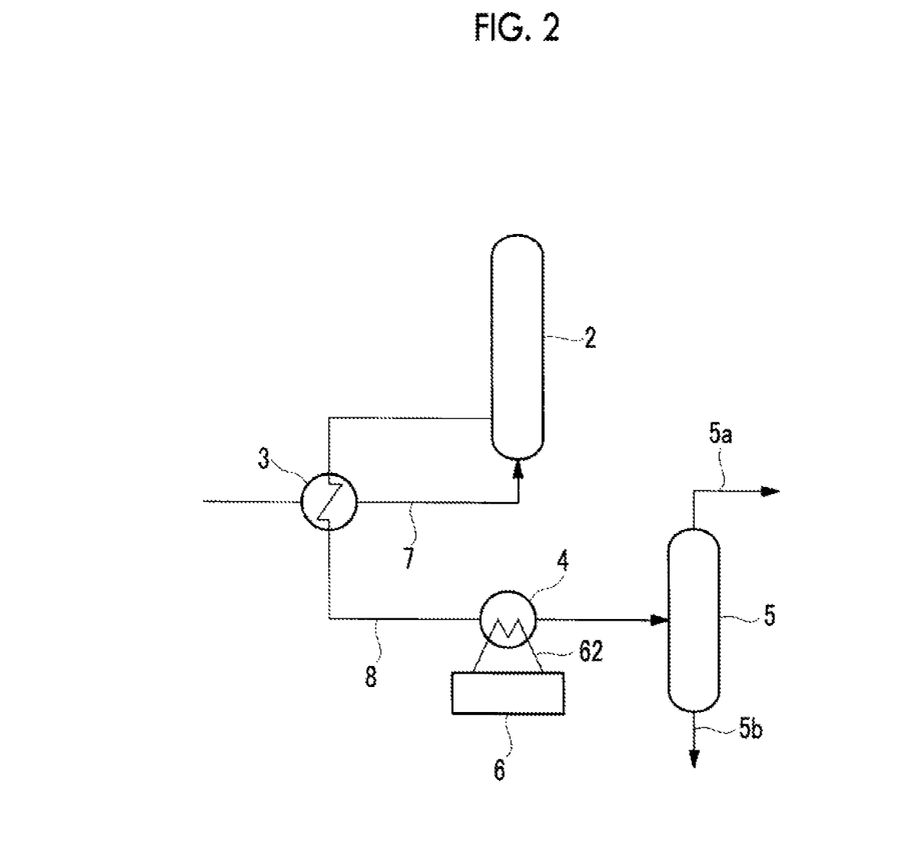
FIG. 2 is a schematic diagram showing a methanol plant to which a seawater desalination device according to the first embodiment of the present invention is applied.

A mixed gas of carbon monoxide and hydrogen generated in the reforming process S2 is taken out of the reformer and compression is performed thereon. The compressed mixed gas is input to a methanol reactor 2 (refer to FIG. 2) (described later) and methanol synthesis is performed like the following formula (a methanol synthesis process S3).

$$CO+2H_2 \rightarrow CH_3OH$$

$$CO_2+3H_2 \rightarrow CH_3OH+H_2O$$

A dimethyl ether synthesis process (not shown) of producing, for example, dimethyl ether by a dehydration reaction of the methanol synthesized in the methanol synthesis process S3 may be provided, as necessary. Further, a methanol to Gasoline (MTG) synthesis process S5 of synthesizing gasoline may be provided. The methanol obtained by methanol synthesis is distilled in, for example, a distillation column (not shown) or the like (a distillation process S4). The distilled methanol is stored by a tank 1.

In the methanol synthesis process S3 (refer to FIG. 1) of synthesizing the mixed gas, as shown in FIG. 2, a mixed gas supply pipe 7 for circulating the compressed mixed gas is connected to a bottom portion of the methanol reactor 2. A mixed gas of methanol synthesized by a synthesis catalyst (not shown) of the methanol reactor 2 and water vapor is produced. A pipe 8 through which the produced mixed gas flows is provided so as to pass through the inside of a methanol separator 3 which performs heat exchange between the mixed gas synthesized by the methanol reactor 2 and the mixed gas before it is supplied to the methanol reactor 2. Further, a heat exchanger 4 to which the pipe 8 is connected and which makes exhaust heat which is discharged from the methanol synthesis process S3 (refer to FIG. 1) be recovered to seawater 61 (refer to FIG. 3) or brine (hereinafter described as seawater) is provided on the downstream side in a mixed gas flow direction. A temperature of the exhaust heat is in a range of 100° C. to 200° C., for example. In the heat exchanger 4, the mixed gas is provided so as to pass through the shell side of the heat exchanger 4. The pipe 8 connected to a mixed gas outlet of the heat exchanger 4 is connected to a gas-liquid separator 5. Pipes 5a and 5b for respectively circulating those separated from the mixed gas are provided at the gas-liquid separator 5. Further, a heat-transfer pipe 62 which is connected to a seawater desalination device 6 is provided in the heat exchanger 4. Water vapor which is produced from fresh water produced in, for example, the seawater desalination device 6 is used in the methanol synthesis process S3.

Figure 3:
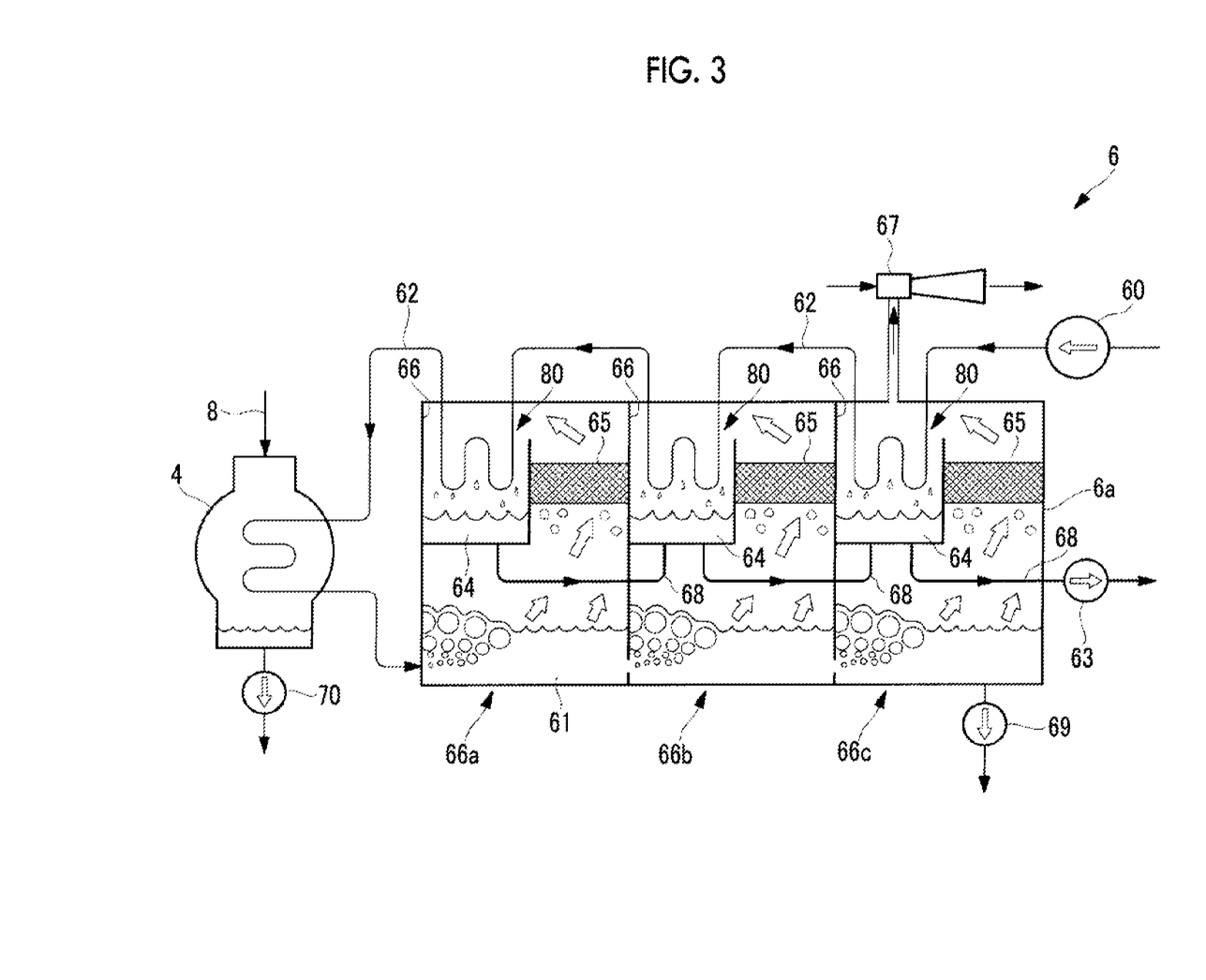
FIG. 3 is a cross-sectional side view showing a schematic configuration of a seawater desalination device which is applied to the methanol plant of FIG. 2.

Next, the seawater desalination device 6 will be described by using FIG. 3. As the seawater desalination device 6, a multistage flash evaporation method using exhaust heat discharged from the methanol synthesis process S3 is used. Flash evaporation is an evaporation method of generating vapor by rapidly lowering the pressure of high-temperature liquid to a saturation pressure or less. The seawater desalination device 6 is provided with a seawater desalination device main body 6a for desalinating the seawater 61, the heat-transfer pipe 62 for supplying the seawater 61 to be desalinate to the seawater desalination device main body 6a, and a pump 60 for conveying the seawater 61 flowing through the heat-transfer pipe 62.

The seawater desalination device main body 6a is a container formed so as to accommodate the seawater 61 and is partitioned into three treatment chambers 66a, 66b, and 66c by partition walls 66 in this embodiment. A demister 65 which captures liquid droplets in vapor and a condenser chamber 80 which collects vapor from which the liquid droplets in vapor are recovered are provided in each of the treatment chambers 66a, 66b, and 66c.

The heat-exchange pipe 62 is provided so as to pass through the condenser chambers 80 of the respective treatment chambers 66a, 66b, and 66c, and a configuration is made such that the seawater 61 flows in the order of the treatment chambers 66a, 66b, and 66c (from the right side in the same drawing). The heat exchanger 4 is provided on the downstream side of the heat-exchange pipe 62, and thus a configuration is made such that the seawater 61 having passed through the respective condenser chambers 80 is heated in the heat exchanger 4.

Each of the treatment chambers 66a, 66b, and 66c which are configured by the partition walls 66 is provided with an ejector 67. The water vapor of each of the treatment chambers 66a, 66b, and 66c is sucked into a negative pressure space (not shown) which is generated inside the ejector 67, whereby pressure reduction is performed. Further, a pipe 68 for extracting fresh water is connected to a lower portion of the condenser chamber 80. The pipe 68 is connected to the suction side of a pump 63 and then sent out to the outside (not shown).

The heat exchanger 4 is connected to the pipe 8. In the pipe 8, the mixed gas flows. Further, a pump 70 for extracting drainage generated when heating the seawater 61 by the heat exchanger 4 is provided. Further, a circulation pump 69 for extracting seawater which has not evaporated is provided at the treatment chamber 66c corresponding to the final stage of the treatment chambers 66a, 66b, and 66c.

Next, an operation of the methanol synthesis process S3 of the methanol plant having the above configuration will be described.

As shown in FIG. 2, carbon dioxide and hydrogen remaining without reaction are included in the mixed gas input to the gas-liquid separator 5. Carbon monoxide, carbon dioxide, and hydrogen are input to the gas-liquid separator 5, whereby methanol and water are separated as liquid and carbon monoxide, carbon dioxide, and hydrogen are separated as gas. The carbon monoxide, the carbon dioxide, and the hydrogen separated in the gas-liquid separator 5 are compressed by a compressor (not shown) and then mixed in the mixed gas of carbon monoxide, carbon dioxide, and hydrogen, which flows through the pipe 7 and is input to the methanol reactor 2. On the other hand, a mixed liquid of the methanol and the water separated in the gas-liquid separator 5 is sent to a distillation column (not shown) and only the methanol is extracted from the mixed liquid of water and methanol in the distillation column.

The mixed gas before it is separated by the gas-liquid separator 5 is heat-exchanged with the seawater 61 flowing through the heat-exchange pipe 62 by the heat exchanger 4. The seawater 61 is heated by the mixed gas and supplied to the heat-transfer pipe 62 passing through the inside of the heat exchanger 4 connected to the seawater desalination device 6, as shown in FIG. 3.

The seawater 61 flowing through the heat-exchange pipe 62 is heated by the heat exchanger 4. The heated seawater 61 is supplied to the seawater desalination device 6 subjected to pressure reduction by the ejector 67. At this time, the pressure in the seawater desalination device 6 is less than or equal to the water vapor saturation pressure of the seawater 61. For this reason, the supplied seawater 61 boils and becomes vapor, thereby evaporating. Liquid droplets in the vapor of the seawater 61 are captured by the demister 65. The vapor after liquid droplets are captured by the demister 65 condenses on the outer surface of the heat-transfer pipe 62 provided so as to pass through the condenser chamber 80, whereby distilled water (fresh water) is produced. For example, in a case where the amount of production of methanol is 2500 t/d, when exhaust heat of 100° C. or more is utilized and the total exhaust heat available for use is $31.5 \times 10^6$ kcal/h, fresh water is produced at 467 t/h. Further, the produced fresh water is extracted by the pump 63.

The seawater 61 remaining in the seawater desalination device 6 is sent back to the side of the pump 60 which supplies the seawater 61 in a cold state to the seawater desalination device 6, by the circulation pump 69.

According to the present invention, the following operation and effects are exhibited.

Exhaust heat is generated in a process of producing methanol as a synthesis gas from natural gas (for example, the methanol synthesis process S3). The heat exchanger 4 which makes the exhaust heat be recovered to the seawater 61 is provided, and heat exchange is performed between the seawater 61 flowing through the heat exchanger 4 and the mixed gas which is in a methanol manufacturing process. The exhaust heat of the mixed gas recovered by the heat exchanger 4 is supplied to the seawater desalination device 6, whereby it is possible to desalinate the seawater 61. In this manner, the exhaust heat is utilized as a heat source of the seawater desalination device 6, whereby it is possible to eliminate costs of fuel which is used in the seawater desalination device 6.

The temperature of the exhaust heat which is recovered by the heat exchanger 4 is in a range of 100° C. to 200° C. The exhaust heat in this temperature range has been discarded without being utilized in the related art. However, by focusing on the fact that the exhaust heat can be effectively utilized when desalinate the seawater 61, a configuration is made such that the exhaust heat is recovered and utilized as a heat source for desalinating the seawater 61. Therefore, it is possible to cool the mixed gas by the seawater 61. Further, it is possible to heat the seawater 61 by the mixed gas. In this way, cooling equipment such as a cooling fan is not required, and therefore, it is possible to reduce the cost of energy or the like for operating a facility.

The exhaust heat obtained from the mixed gas is supplied to the seawater desalination device 6 using a multistage flash evaporation method. In this way, it is possible to obtain fresh water from the seawater 61. Since it is not necessary to manufacture a heat source (for example, heating steam) for evaporating seawater, it is possible to eliminate fuel costs. Further, since it is not necessary to burn fuel (for example, fossil fuel), it is possible to prevent the generation of carbon dioxide in a seawater desalination process.

Second Embodiment

Figure 4:
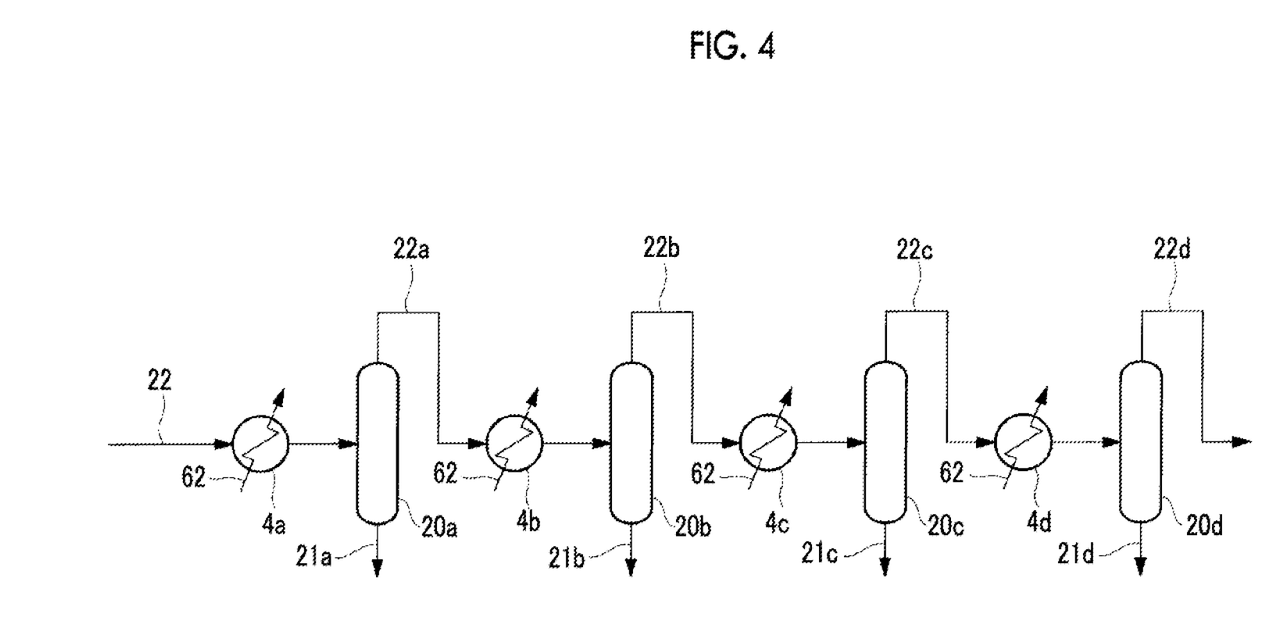
FIG. 4 is a schematic diagram showing a methanol plant according to a second embodiment of the present invention.

Next, a second embodiment of the present invention will be described by using FIG. 4.

This embodiment is configured such that the heat exchanger 4 shown in the first embodiment is provided in the distillation process S4 of a methanol plant having the MTG synthesis process S5. Therefore, the same configurations as those in the first embodiment are the same reference numerals and description thereof is omitted.

In a case where a methanol plant (a gasoline synthesis plant) has the MTG synthesis process S5, a place which does not need the methanol distillation process S4 exists. As shown in FIG. 4, a pipe 22 through which a mixed gas flows is connected to a distillation column reboiler 20*a*. A heat source for distilling the mixed gas is supplied to a distillation column (not shown) by each of the distillation column reboilers 20*a* to 20*d*. For example, the distillation column reboilers 20*a*, 20*b*, 20*c*, and 20*d* are provided in the pipe 22. Pipes 22*a*, 22*b*, 22*c*, and 22*d* into which the distilled mixed gas flows are respectively provided at upper portions of the distillation column reboilers 20*a* to 20*d*. Further, discharge pipes 21*a*, 21*b*, 21*c*, and 21*d* which discharge drainage condensed by the mixed gas are respectively provided at bottom portions of the distillation column reboilers 20*a* to 20*d*. Heat exchangers 4*b* to 4*d* which are located on the upstream side are respectively provided at the sides of the distillation column reboilers 20*a* to 20*c* such that the mixed gas flows therethrough.

In a case where the methanol plant has the MTG synthesis process S5, as in this embodiment, the MTG synthesis process S5 is provided instead of the methanol distillation process S4 described in the first embodiment. Because of this, the heat exchangers 4*a*, 4*b*, 4*c*, and 4*d* for recovering exhaust heat which is used in the distillation column reboilers 20*a* to 20*d* of the MTG synthesis process S5 are provided. The heat-transfer pipe 62 which is connected to the seawater desalination device 6 is connected to each of the heat exchangers 4*a* to 4*d* so as to pass therethrough.

The exhaust heat which is not used in the heating of a distillation column (not shown) in the respective distillation column reboilers 20*a* to 20*d* is recovered by the respective heat exchangers 4*a* to 4*d*. The recovered exhaust heat is supplied to the seawater desalination device 6 (refer to FIG. 3). Further, the temperature of the mixed gas decreases as it goes toward the downstream side in the flow direction of the mixed gas flowing through the respective pipes 22*a* to 22*d*. In a case where the gas temperature decreases, the gas temperature falls below the dew points of some components in the gas, and therefore, the wetness of the gas increases as it flows toward the downstream side in the gas flow direction.

According to this embodiment, the exhaust heat which becomes unnecessary in the MTG synthesis process S5 can be recovered by the heat exchangers 4*a* to 4*d*. The exhaust heat is supplied to the seawater desalination device 6, whereby it is possible to effectively use the exhaust heat. Therefore, it is possible to eliminate costs of fuel needed to heat the seawater 61 (refer to FIG. 3).

Further, according to this embodiment, the methanol distillation process S4 of distilling methanol is not required in a case of having the MTG synthesis process S5. Therefore, the exhaust heat having been used in the methanol distillation process S4 can be supplied to the seawater desalination device 6. In this way, it is possible to produce a large amount of fresh water, as compared to the methanol plant having the methanol distillation process S4. Further, it is possible to not only supply fresh water which is required in the methanol synthesis process S3, but also supply fresh water to a peripheral area which is poor in a water source. Further, in a case of having the MTG synthesis process S5, for example, when the amount of production of methanol is 2500 t/d and the methanol is converted into gasoline, the total exhaust heat available for use is $59.7 \times 10^6$ kcal/h and the amount of production of fresh water is 886 t/h.

Further, according to this embodiment, it is possible to perform heat exchange with gas having higher wetness as it goes toward the heat exchanger 4 (for example, the heat exchanger 4*d*) provided on the downstream side in the flow direction of the gas which is in the MTG synthesis process S5. As compared to a case of performing heat exchange between a dry gas having wetness of 0 and the seawater 61, the wettability of the heat-exchange pipe 62 provided in each of the heat exchangers 4*a* to 4*d* increases, and thus it is possible to improve a heat transfer property. Therefore, a heat transfer property can be improved as it approaches the downstream side in the flow direction of the gas which is in the MTG synthesis process S5. In this way, it is possible to improve exhaust heat recovery efficiency. Further, it is possible to improve heat exchange efficiency, and therefore, it is possible to reduce the sizes of the heat exchangers 4*a* to 4*d*.

REFERENCE SIGNS LIST

1: tank
2: methanol reactor
3: methanol separator
4: heat exchanger
4*a*, 4*b*, 4*c*, 4*d*: heat exchanger
5: gas-liquid separator
5*a*, 5*b*: pipe
6: seawater desalination device
7: mixed gas supply pipe
8: pipe
20*a*, 20*b*, 20*c*, 20*d*: distillation column reboiler
62: heat-transfer pipe

The invention claimed is:

1. A methanol plant comprising:
   a heat exchanger which makes exhaust heat that is discharged from a process of producing methanol from a feed stock be recovered to seawater; and
   a seawater desalination device which obtains fresh water from the seawater by using the exhaust heat recovered from the seawater by the heat exchanger,
   wherein a plurality of the heat exchangers is provided in a distillation process of the process of producing methanol in a flow direction of mixed gas after methanol synthesis,
   wherein the mixed gas passes through the plurality of heat exchangers, and a temperature of the mixed gas decreases, and a wetness of the mixed gas increases as it flows toward a downstream side in the flow direction of the mixed gas, and
   wherein heat exchange with the mixed gas having increased wetness is performed in the heat exchanger provided on a downstream side in the flow direction of the mixed gas.

2. The methanol plant according to claim 1, wherein the exhaust heat has a temperature in a range of 100° C. to 200° C.

3. The methanol plant according to claim 2, wherein the seawater desalination device obtains the fresh water by a multistage flash evaporation method using the exhaust heat.

4. The methanol plant according to claim 2, wherein the methanol is produced by using vapor which is produced from the fresh water.

5. The methanol plant according to claim 2, wherein the process is provided with a step of producing gasoline from the methanol.

6. The methanol plant according to claim 1, wherein the seawater desalination device obtains the fresh water by a multistage flash evaporation method using the exhaust heat.

7. The methanol plant according to claim 6, wherein the methanol is produced by using vapor which is produced from the fresh water.

8. The methanol plant according to claim 6, wherein the process is provided with a step of producing gasoline from the methanol.

9. The methanol plant according to claim 1, wherein the methanol is produced by using vapor which is produced from the fresh water.

10. The methanol plant according to claim 9, wherein the process is provided with a step of producing gasoline from the methanol.

11. The methanol plant according to claim 1, wherein the process is provided with a step of producing gasoline from the methanol.

12. A gasoline synthesis plant comprising:
    a methanol plant which produces methanol from a feed stock;
    a heat exchanger which makes exhaust heat that is discharged from a process of producing gasoline from the methanol be recovered to seawater; and
    a seawater desalination device which obtains fresh water from the seawater by using the exhaust heat recovered by the seawater.

* * * * *